US006846948B2

(12) United States Patent
Riondel et al.

(10) Patent No.: US 6,846,948 B2
(45) Date of Patent: Jan. 25, 2005

(54) PROCESS FOR PREPARING BUTYL ACRYLATE BY DIRECT ESTERIFICATION

(75) Inventors: Alain Riondel, Forbach (FR); Jacqueline Bessalem, Saint Avold (FR)

(73) Assignee: Arkema, Puteaux (FR)

( * ) Notice: Subject to any disclaimer, the term of this patent is extended or adjusted under 35 U.S.C. 154(b) by 0 days.

(21) Appl. No.: 10/411,379

(22) Filed: Apr. 11, 2003

(65) Prior Publication Data

US 2003/0220519 A1 Nov. 27, 2003

(30) Foreign Application Priority Data

Apr. 11, 2002 (FR) .............................................. 02 04506

(51) Int. Cl.⁷ .............................................. C07C 69/52
(52) U.S. Cl. ..................................................... 560/205
(58) Field of Search ................................. 560/205, 218

(56) References Cited

U.S. PATENT DOCUMENTS

| 4,698,440 A | | 10/1987 | Blair et al. | |
| 5,659,072 A | * | 8/1997 | Bessalem et al. | ............ 560/218 |
| 6,025,520 A | | 2/2000 | Suzuki et al. | |

FOREIGN PATENT DOCUMENTS

EP 0 202 610 A2 11/1986

OTHER PUBLICATIONS

Patent Abstract of Japan, vol. 1998, No. 12, Oct. 31, 1998 & JP 10 182554 A (Asahi Chem Ind Co Ltd), Jul. 7, 1996.

* cited by examiner

*Primary Examiner*—Paul A. Zucker
(74) *Attorney, Agent, or Firm*—Millen, White, Zelano & Branigan, P.C.

(57) ABSTRACT

Butyl acrylate is prepared by reacting acrylic acid and butanol in a reactor in the presence of an esterification catalyst the water formed being entrained by distillation in a column (2) in the form of a heteroazeotropic mixture with butanol mixture following condensation, being separated in a decanter (3) to give an upper, organic phase which is recycled to the top of the distillation column (2) and a lower, aqueous phase which is drawn off. The reaction is conducted with deferred introduction of part of the butanol at the top of the distillation column (2) or to the decanter (3) or to the reactor (1), the butanol/acrylic acid molar ratio being initially between 0.5 and 1 before rising to between 1 and 1.5 following the completion of the deferred introduction of the butanol.

25 Claims, 1 Drawing Sheet

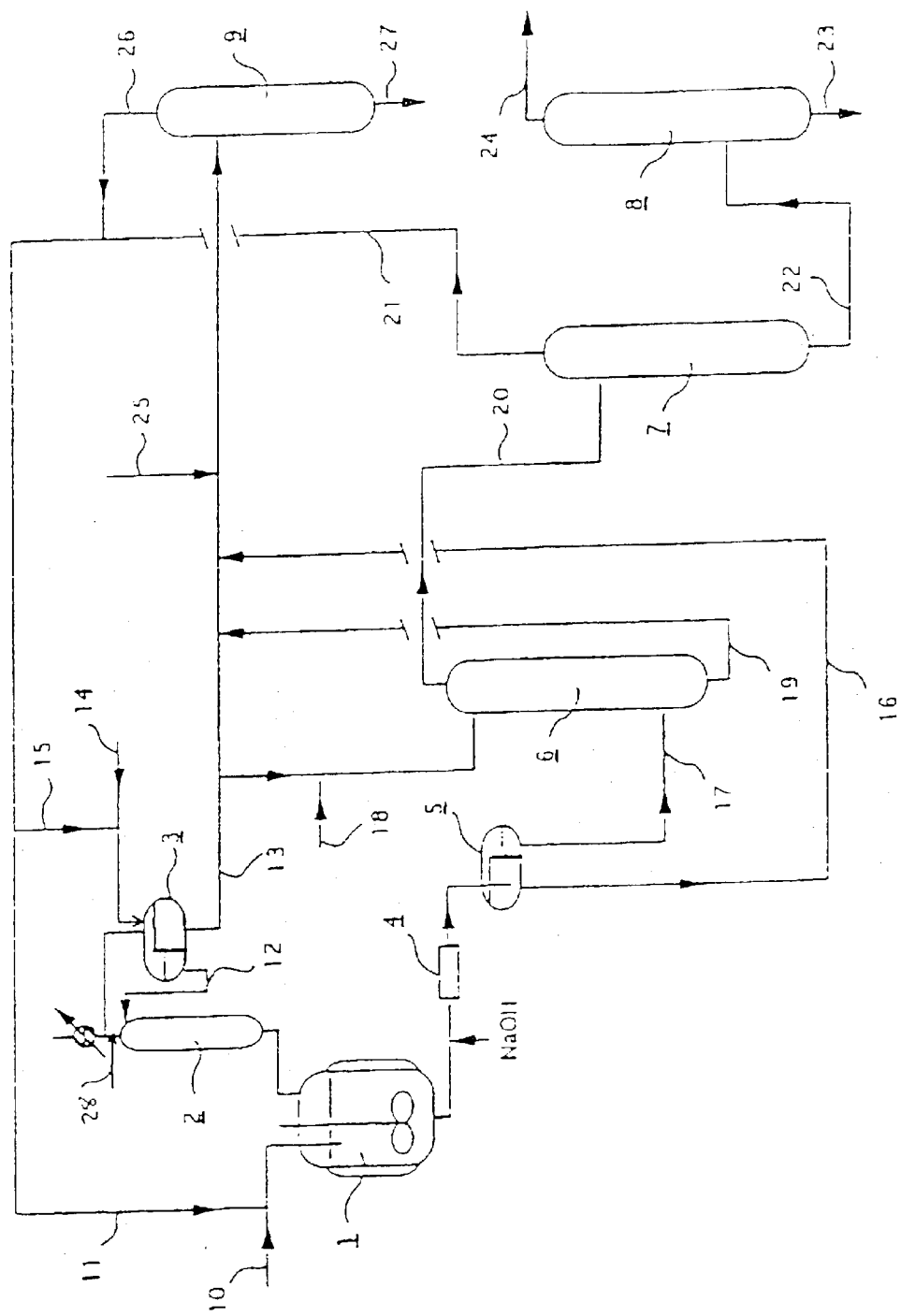

PROCESS FOR PREPARING BUTYL ACRYLATE BY DIRECT ESTERIFICATION

The present invention relates to a process for preparing butyl acrylate by reacting acrylic acid and butanol in a reactor in the presence of preferably an acid as esterification catalyst and preferably of at least one polymerization inhibitor, the water formed by the reaction being entrained by distillation into a column in the form of a heteroazeotropic mixture with butanol and the heteroazeotropic mixture being subsequently subjected, following condensation, to separation in a decanter to give an upper, organic phase which is recycled to the top of the distillation column and a lower, aqueous phase which is drawn off.

In the course of this reaction there are secondary reactions, including the formation of butyl butoxypropionate (BBP) by Michael addition of the butanol onto the double bond of the butyl acrylate.

Since BBP represents from 70 to 90% of the total impurities, an object of this invention is to reduce specifically the formation of BBP without adversely affecting the reaction kinetics. Upon further study of the specification and appended claims, other objects and advantages will become apparent.

Conditions have been found for limiting the formation of BBP which at the same time allow productivity to be augmented. These conditions constitute the novel and inventive features of the process of the present invention.

The process as defined above is characterized in that the reaction is conducted:

- with deferred (delayed) introduction of part of the butanol at the top of the distillation column or into the decanter or into the reactor, the butanol/acrylic acid molar ratio into the reactor being initially between 0.5 and 1, preferably less than 1,
- before rising to between 1 and 1.5 following completion of the deferred introduction of the butanol the difference between the initial and final molar ratios being preferably at least 0.1 and more preferably at least 0.2;
- with an initial temperature (Ti) at the reactor bottom whose lower limit is 70° C. and a final temperature (Tf) at the reactor bottom which is greater than (Ti) and whose upper limit is 110°; and
- under an initial pressure (Pi) of from $3.33 \times 10^4$ Pa (250 mmHg) to $1.33 \times 10^4$ Pa (100 mmHg) and a final pressure (Pf) of from $2.66 \times 10^4$ Pa (200 mmHg) to $0.66 \times 10^4$ Pa (50 mmHg).

In a preferred feature of the invention the total mass of butanol is introduced when 85% of the expected mass of water of reaction has been drawn off.

In accordance with a first embodiment of the process of the invention the deferred introduction of the butanol takes place into the decanter and it is recycled to the top of the distillation column. The upper, organic phase of the decanter can be returned to the top of the distillation column by natural overflow.

In accordance with a second embodiment of the process of the invention the deferred introduction of the butanol takes place directly into the top of the distillation column.

The deferred introduction of the butanol advantageously takes place continuously, it being possible for the rate of deferred introduction of the butanol to be equal to the rate of withdrawal of the water of reaction.

The esterification reaction is conducted preferably with an initial butanol/acrylic acid molar ratio of 0.92 which rises to 1.12 following completion of the deferred introduction of butanol.

In accordance with one particular embodiment the reaction is conducted with an initial temperature (Ti) of 80° C. for 30 minutes with regulation of the pressure which varies from $2.933 \times 10^4$ Pa to $2.266 \times 10^4$ Pa and then, while maintaining this pressure, the temperature is allowed to develop until Tf=100° C.

BRIEF DESCRIPTION OF DRAWING

The single FIGURE of the attached drawing is a flowsheet of one particular embodiment of the process of the invention, which will be described hereinbelow.

Referring to the single FIGURE of the attached drawing it can be seen that the reactor 1, surmounted with a distillation column 2, is charged batchwise with fresh acrylic acid, fresh butanol, the stabilizers and the catalyst ($H_2SO_4$) via line 10 and via line 11 with the flow of light compounds (essentially butanol and butyl acrylate) recovered in the downstream topping columns 7 and 9. The temperature of the reaction medium is between 70 and 110° C. under a reduced pressure which is such as to maintain the desired temperature. During the reaction a mixture of butanol, butyl acrylate and water is distilled which separates, following condensation, into two phases in the decanter 3. The organic phase 12 is returned by overflow to the head of column 2 while the aqueous phase 13 is sent to the feed of the distillation column 9 and/or to the top of the scrubbing column 6. During the reaction a flow of fresh butanol and/or of light compounds 15 recovered in the topping columns 7 and 9 is introduced alternatively

- into the decanter 3 via line 14; or
- at the top of column 2 via line 28; or
- into the reactor via line 10 (the butanol charging line is used to introduce the deferred butanol).

Following reaction, the crude reaction product is neutralized with aqueous sodium hydroxide solution in the mixer 4 in order to remove the catalyst and/or the residual acrylic acid. The heterogeneous mixture is separated in the decanter 5 into an aqueous phase 16, which is sent to the feed of the column 9, and an organic phase, which constitutes the feed 17 to the bottom of the scrubbing column 6.

This scrubbing column 6 is, moreover, supplied at the top with demineralized water 18 and/or with all or part of the water of reaction 13. At the bottom of column 6 an alkaline aqueous flow 19 is recovered, which rejoins the feed of column 9.

At the top of column 6 the neutralized and washed crude product 20 is sent to the topping column 7, which allows the excess butanol and some butyl acrylate to be recovered at the top. This mixture 21 is recycled to the reaction step via the line 11.

The topped crude product 22 recovered at the bottom of the column 7 feeds the tailing column 8, which removes the heavy fractions 23 at the bottom, to give the pure ester 24 at the top.

All the aqueous phases of the plant—reaction water 13, water for neutralizing the crude product 16, water from the washing column 19, and other plant waters 25—are sent to column 9, at the top (26) of which the butanol is principally recovered, and is recycled to the reaction step via the pipe 11. The waste waters 27, freed of most of the pollutant organic products, are removed for subsequent biological treatment prior to discharge.

The present invention will now be further illustrated by the following, non-limiting examples. In these examples the percentages are by weight, unless indicated otherwise, and the following abbreviations have been used:

AA: acrylic acid
BuOH: butanol
BuA: butyl acrylate
BBP: butyl butoxypropionate
PTZ: phenothiazine
GC: gas chromatography
Apparatus All the examples were carried out in an apparatus consisting of:

- a jacketed reactor with a capacity of 1 liter, equipped with a mechanical stirrer, a temperature probe and a dip tube for the introduction of air into the reaction medium and a pipe allowing a portion of the butanol to be introduced, where appropriate; this reactor is surmounted with a distillation column;
- two pipes allowing a portion of the butanol intended for esterification to be sent, where appropriate, either to the top of the column or to the decanter;
- a condenser which is supplied with glycol-containing water and is held at a temperature of 0° C.;
- a probe for measuring the temperature at the top of the column;
- a decanter which collects a BuA/BuOH/$H_2O$ mixture, which separates into a lower, aqueous phase, which is removed at the same rate as it is formed, and an upper, organic phase, which is returned to the top by natural overflow;
- a regulated vacuum system which permits operation under reduced pressure.

MODE OF OPERATION ACCORDING TO THE INVENTION

The reactor is charged with acrylic acid, the phenothiazine stabilizer (0.07%/charge), 96% sulphuric acid (1%/charge), and the BuA/BuOH mixture from the topping column. The initial BuOH/AA molar ratio is set at 0.92.

The final BuOH/AA molar ratio is 1.12. It is obtained by adding butanol
either to the decanter (Example 1)
or continuously at the top of the column (Example 2).

EXAMPLE 1

Inventive

The mixture is heated to 80° C. and the process is operated at this temperature for approximately 30 minutes with regulation of the pressure, which varies from $2.933 \times 10^4$ Pa (220 mmHg) to $2.266 \times 10^4$ Pa (170 mmHg). Then, at $2.266 \times 10^4$ Pa (170 mmHg), the temperature is allowed to develop until it reaches 100° C. Throughout the reaction the water of reaction is removed by distillation of the BuA/BuOH/water hetero-azeotrope. The rate of introduction of the butanol into the decanter is equal to the rate of withdrawal of the water of reaction, the butanol being added over 80 minutes. The total mass of butanol introduced deferredly is introduced when approximately 85% of the expected mass of water of reaction has been drawn off. The reaction is considered over when the AA content of the reaction medium reaches 0.5%. The crude reaction product is cooled and then neutralized with 8% sodium hydroxide solution in order to remove the catalyst. The organic phase is analysed by GC to determine the BuA and BBP contents, from which it is possible to determine the BBP/BuA ratio×100 and the productivity expressed in g of BuA formed/h/$cm^3$ volume of the initial charge.

The results obtained are indicated in Table 1.

EXAMPLE 2

Inventive

The conditions of Example 1 were reproduced except that the butanol added deferredly is introduced at the top of the column over a period of 80 minutes. The results obtained are likewise indicated in Table 1.

TABLE 1

| EXAMPLE | 1 | 2 |
| --- | --- | --- |
| Reactor charge* | | |
| BuOH (moles) | 4.2 | 5.35 |
| AA (moles) | 4.55 | 5.8 |
| BuA (mole) | 0.32 | 0.39 |
| $H_2O$ (mole) | 0.21 | 0.7 |
| BuOH introduced (moles) | 0.89 | 1.13 |
| Initial BuOH/AA molar ratio | 0.92 | 0.92 |
| Final BuOH/AA molar ratio | 1.12 | 1.12 |
| Reaction | | |
| Initial pressure in Pa (mmHg) | $2.933 \times 10^4$ (220) | $2.933 \times 10^4$ (220) |
| Final pressure in Pa (mmHg) | $2.266 \times 10^4$ (170) | $2.266 \times 10^4$ (170) |
| Temperature at reactor bottom (° C.) | 80 to 100 | 80 to 100 |
| Reaction time | 2 h 40 min | 2 h 40 min |
| Crude product at 25° C. | | |
| Residual AA in crude product (%) | 0.27 | 0.14 |
| BBP/BuA (%) | 2.13 | 2.64 |
| Productivity (g/h/$cm^3$) | 0.28 | 0.28 |

*not including $H_2SO_4$ and PTZ

COMPARATIVE EXAMPLES 3 TO 10

In these examples the temperature and the BuOH/AA molar ratio were varied (Examples 3, 4, 5, 6, 7, 9 and 10). The process was also carried out with a variable molar ratio, with an initial molar ratio not equal to 0.92 (Example 8).

In no case did the resultant proportions of BBP/BuA and the resultant productivity attain simultaneously the performance levels obtained in Examples 1 and 2.

The results are given in Table 2.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosure of all applications, patents and publications, cited herein and of corresponding French application No. 02/04506, filed Apr. 11, 2002 is incorporated by reference herein.

TABLE 2

| COMPARATIVE EXAMPLE | 3 | 4 | 5 | 6 | 7 | 8 | 9 | 10 |
|---|---|---|---|---|---|---|---|---|
| Reactor charge* | | | | | | | | |
| BuOH (moles) | 6.5 | 6.5 | 6.5 | 6.5 | 6.5 | 5.81 | 6.5 | 6.5 |
| AA (moles) | 5 | 5 | 5 | 5.81 | 5.81 | 5.81 | 5.81 | 5.81 |
| BuA (moles) | 0.39 | 0.39 | 0.39 | 0.39 | 0 | 0.39 | 0.39 | 0.39 |
| H₂O (mole) | 0.7 | 0.7 | 0.7 | 0.7 | 0 | 0.7 | 0.7 | 0.7 |
| BuOH introduced (mole) | 0 | 0 | 0 | 0 | 0 | 0.69 | 0 | 0 |
| Initial BuOH/AA molar ratio | 1.3 | 1.3 | 1.3 | 1.12 | 1.12 | 1 | 1.12 | 1.3 |
| Final BuOH/AA molar ratio | 1.3 | 1.3 | 1.3 | 1.12 | 1.12 | 1.12 | 1.12 | 1.3 |
| Reaction | | | | | | | | |
| Initial pressure in Pa (mmHg) | 2.933 (220) | 7.066 (530) | 8.266 (620) | 8.266 (620) | 5.333 (400) | 8.266 (620) | 8.266 (620) | 5.333 (400) |
| Final pressure $10^4$ Pa (mmHg) | 1.387 (104) | 2.960 (222) | 1.440 (108) | 2.480 (186) | 1.720 (129) | 2.453 (184) | 1.200 (90) | 1.413 (106) |
| Temperature at reactor bottom (° C.) | 80 | 100 | 100° C.: 1 h 10 80° C.: 1 h 40 | 100 | 90 | 100 | 100° C.: 1 h 15 80° C.: 2 h 15 | 90 |
| Reaction time | 3 h 30 | 2 h | 2 h 50 | 2 h 20 | 3 h 15 | 2 h 40 | 3 h 30 | 2 h 25 |
| Crude product at 25° C. | | | | | | | | |
| Residual AA in crude product (%) | 0.13 | 0.11 | 0.05 | 0.11 | 0.2 | 0.35 2.84 | 0.19 | 0.12 |
| BBP/BuA (%) | 2.12 | 3.44 | 3.78 | 3.05 | 2.66 | | 2.86 | 3.02 |
| Productivity (g/h/cm³) | 0.17 | 0.30 | 0.21 | 0.28 | 0.21 | 0.25 | 0.19 | 0.25 |

*not including $H_2SO_4$ and PTZ

What is claimed is:

1. A process for preparing butyl acrylate comprising:
reacting acrylic acid and butanol in a reactor in the presence of an esterification catalyst wherein the water formed by the reaction is entrained by distillation in a distillation column in the form of a heteroazeotropic mixture with butanol;
subjecting the heteroazeotropic mixture, following condensation, to separation in a decanter to yield an upper, organic phase which is recycled to the top of the distillation column and a lower, aqueous phase which is drawn off,
wherein the reaction is conducted:
with deferred introduction of part of the butanol at the top of the distillation column or into the decanter or into the reactor, the butanol/acrylic acid molar ratio being initially between 0.5 and 1 before rising to between 1 and 1.5 following completion of the deferred introduction of the butanol;
with an initial temperature, Ti, at the reactor bottom whose lower limit is 70° C. and a final temperature, Tf, at the reactor bottom which is greater than Ti and whose upper limit is 110°; and
under an initial pressure, Pi, of from $3.33 \times 10^4$ Pa to $1.33 \times 10^4$ Pa and a final pressure, Pf, of from $2.66 \times 10^4$ Pa to $0.66 \times 10^4$ Pa.

2. A process according to claim 1, wherein the total mass of butanol is introduced when 85% of the expected mass of water of reaction has been drawn off.

3. A process according to claim 1, wherein the deferred introduction of the butanol takes place in the decanter and the butanol is then recycled to the top of the distillation column.

4. A process according to claim 3, wherein the upper, organic phase of the decanter is returned to the top of the distillation column by natural overflow.

5. A process according to claim 1, wherein the deferred introduction of the butanol takes place directly into the top of the distillation column.

6. A process according to claim 1, wherein the deferred introduction of the butanol takes place continuously.

7. A process according to claim 6, wherein the rate at which butanol is introduced is equal to the rate at which water of reaction is drawn off.

8. A process according to claim 1, wherein the esterification reaction is conducted with an initial butanol/acrylic acid molar ratio of 0.92 which rises to 1.12 following completion of the deferred introduction of butanol.

9. A process according to claim 1, wherein the reaction is conducted with a Ti of 80° C. for 30 minutes with regulation of the pressure which varies from $2.933 \times 10^4$ Pa to $2.266 \times 10^4$ Pa and then, while maintaining this pressure, the temperature is allowed to develop to Tf=100° C.

10. A process according to claim 2, wherein the deferred introduction of the butanol takes place in the decanter and the butanol is then recycled to the top of the distillation column.

11. A process according to claim 1, wherein the upper, organic phase of the decanter is returned to the top of the distillation column by natural overflow.

12. A process according to claim 2, wherein the deferred introduction of the butanol takes place directly into the top of the distillation column.

13. A process according to claim 2, wherein the esterification reaction is conducted with an initial butanol/acrylic acid molar ratio of 0.92 which rises to 1.12 following completion of the deferred introduction of butanol.

14. A process according to claim 3, wherein the esterification reaction is conducted with an initial butanol/acrylic acid molar ratio of 0.92 which rises to 1.12 following completion of the deferred introduction of butanol.

15. A process according to claim 4, wherein the esterification reaction is conducted with an initial butanol/acrylic acid molar ratio of 0.92 which rises to 1.12 following completion of the deferred introduction of butanol.

16. A process according to claim 5, wherein the esterification reaction is conducted with an initial butanol/acrylic acid molar ratio of 0.92 which rises to 1.12 following completion of the deferred introduction of butanol.

17. A process according to claim 6, wherein the esterification reaction is conducted with an initial butanol/acrylic acid molar ratio of 0.92 which rises to 1.12 following completion of the deferred introduction of butanol.

18. A process according to claim 7, wherein the esterification reaction is conducted with an initial butanol/acrylic acid molar ratio of 0.92 which rises to 1.12 following completion of the deferred introduction of butanol.

19. A process according to claim 10, wherein the esterification reaction is conducted with an initial butanol/acrylic acid molar ratio of 0.92 which rises to 1.12 following completion of the deferred introduction of butanol.

20. A process according to claim 11, wherein the esterification reaction is conducted with an initial butanol/acrylic acid molar ratio of 0.92 which rises to 1.12 following completion of the deferred introduction of butanol.

21. A process according to claim 12, wherein the esterification reaction is conducted with an initial butanol/acrylic acid molar ratio of 0.92 which rises to 1.12 following completion of the deferred introduction of butanol.

22. A process according to claim 1, wherein the butanol/acrylic acid molar ratio is initially less than 1.

23. A process according to claim 1, wherein the difference between the initial and final butanol/acrylic acid molar ratios is at least 0.1.

24. A process according to claim 1, wherein the difference between the initial and final butanol/acrylic acid molar ratios is at least 0.1.

25. A process according to claim 1, wherein the difference between the initial and final butanol/acrylic acid molar ratios is at least 0.2.

* * * * *